United States Patent
Sun et al.

(10) Patent No.: US 7,250,493 B2
(45) Date of Patent: Jul. 31, 2007

(54) FC FUSION PROTEINS OF HUMAN ERYTHROPOIETIN WITH INCREASED BIOLOGICAL ACTIVITIES

(76) Inventors: Lee-Hwei K. Sun, 4212 Villanova, Houston, TX (US) 77005; Bill N. C. Sun, 4901 Welford, Bellaire, TX (US) 77401; Cecily R. Y. Sun, 4901 Welford, Bellaire, TX (US) 77401

( * ) Notice: Subject to any disclaimer, the term of this patent is extended or adjusted under 35 U.S.C. 154(b) by 149 days.

(21) Appl. No.: 11/017,185

(22) Filed: Dec. 17, 2004

(65) Prior Publication Data

US 2005/0142642 A1   Jun. 30, 2005

(51) Int. Cl.
*C07K 16/46*    (2006.01)
*C07K 14/505*   (2006.01)
*C12N 5/06*     (2006.01)
*C12N 15/00*    (2006.01)

(52) U.S. Cl. .................. 530/387.3; 530/397; 435/69.1; 435/325; 435/328; 435/335

(58) Field of Classification Search ..................... None
See application file for complete search history.

*Primary Examiner*—Marianne P. Allen
*Assistant Examiner*—Regina M. DeBerry
(74) *Attorney, Agent, or Firm*—The Sun Law Office; Hsiang-ning Sun

(57) ABSTRACT

Fc fusion proteins of human EPO with increased biological activities relative to rHuEPO on a molar basis are disclosed. The HuEPO-L-vFc fusion protein comprises HuEPO, a flexible peptide linker of about 20 or fewer amino acids, and a human IgG Fc variant. The Fc variant is of a non-lytic nature and shows minimal undesirable Fc-mediated side effects. A method is also disclosed to make or produce such fusion proteins at high expression levels. Such HuEPO-L-vFc fusion proteins exhibit extended serum half-life and increased biological activities, leading to improved pharmacokinetics and pharmacodynamics, thus fewer injections will be needed within a period of time.

12 Claims, 5 Drawing Sheets

Amino acid sequence alignment in human IgG isotypes and their variants.

| Human IgG Isotype | Amino Acid Position | | | | |
|---|---|---|---|---|---|
| | 228......234 | 235 | 236 | 237......330 | 331 |
| G1 | Pro......Leu | Leu | Gly | Gly......Ala | Pro |
| G2 | Pro......Val | Ala | ......... | Gly......Ala | Pro |
| G4 | Ser......Phe | Leu | Gly | Gly......Ser | Ser |
| G1 variant | Pro......Val | Ala | Gly | Gly......Ala | Ser |
| G2 variant | Pro......Val | Ala | ......... | Gly......Ala | Ser |
| G4 variant | Pro......Phe | Ala | Gly | Gly......Ser | Ser |

| ID number | Corresponding Row |
|---|---|
| SEQ ID NO:26 | G1 |
| SEQ ID NO:27 | G2 |
| SEQ ID NO:28 | G4 |
| SEQ ID NO:22 | G1 variant |
| SEQ ID NO:18 | G2 variant |
| SEQ ID NO:20 | G4 variant |

*FIG 1*

DNA and deduced amino acid sequences of HuEPO-L-vFcγ2

DNA                SEQ NO. 17
Amino Acid Sequence SEQ NO. 18

```
aag ctt ggc gcg gag atg ggg gtg cac gaa tgt cct gcc tgg ctg tgg ctt ctc ctg tcc   60
HindIII              M   G   V   H   E   C   P   A   W   L   W   L   L   L   S
                    -27                                 -20
ctg ctg tcg ctc cct ctg ggc ctc cca gtc ctg ggc gcc cca cca cgc ctc atc tgt gac  120
 L   L   S   L   P   L   G   L   P   V   L   G   A   P   P   R   L   I   C   D
            -10                                  -1   1
agc cga gtc ctg gag agg tac ctc ttg gag gcc aag gag gcc gag aat atc acg acg ggc  180
 S   R   V   L   E   R   Y   L   L   E   A   K   E   A   E   N   I   T   T   G
        10                                  20
tgt gct gaa cac tgc agc ttg aat gag aat atc act gtc cca gac acc aaa gtt aat ttc  240
 C   A   E   H   C   S   L   N   E   N   I   T   V   P   D   T   K   V   N   F
        30                                  40
tat gcc tgg aag agg atg gag gtc ggg cag cag gcc gta gaa gtc tgg cag ggc ctg gcc  300
 Y   A   W   K   R   M   E   V   G   Q   Q   A   V   E   V   W   Q   G   L   A
        50                                  60
ctg ctg tcg gaa gct gtc ctg cgg ggc cag gcc ctg ttg gtc aac tct cca cag ccg tgg  360
 L   L   S   E   A   V   L   R   G   Q   A   L   L   V   N   S   Q   P   W
        70                                  80
gag ccc ctg cag ctg cat gtg gat aaa gcc gtc agt ggc ctt cgc agc ctc acc act ctg  420
 E   P   L   Q   L   H   V   D   K   A   V   S   G   L   R   S   L   T   T   L
        90                                  100
ctt cgg gct ctg gga gcc cag aag gaa gcc atc tcc cct cca gat gcg gcc tca gct gct  480
 L   R   A   L   G   A   Q   K   E   A   I   S   P   P   D   A   A   S   A   A
       110                                  120
cca ctc cga aca atc act gct gac act ttc cgc aaa ctc ttc cga gtc tac tcc aat ttc  540
 P   L   R   T   I   T   A   D   T   F   R   K   L   F   R   V   Y   S   N   F
       130                                  140
ctc cgg gga aag ctg aag ctg tac aca ggg gag gcc tgc agg aca ggg gac gga tcc ggt  600
 L   R   G   K   L   K   L   Y   T   G   E   A   C   R   T   G   D   G   S   G
       150                                  160
ggc ggt tcc ggt gga ggc gga agc ggc ggt gga tca gag cgc aaa tgt tgt gtc gag  660
 G   G   S   G   G   G   G   S   G   G   G   S   E   R   K   C   C   V   E
       170                                  180
tgc cca ccg tgc cca gca cca cct gtg gca gga ccg tca gtc ttc ctc ttc ccc cca aaa  720
 C   P   P   C   P   A   P   P   V   A   G   P   S   V   F   L   F   P   P   K
       190                                  200
ccc aag gac acc ctc atg atc tcc cgg acc cct gag gtc acg tgc gtg gtg gtg gac gtg  780
 P   K   D   T   L   M   I   S   R   T   P   E   V   T   C   V   V   V   D   V
       210                                  220
agc cac gaa gac ccc gag gtc cag ttc aac tgg tac gtg gac ggc gtg gag gtg cat aat  840
 S   H   E   D   P   E   V   Q   F   N   W   Y   V   D   G   V   E   V   H   N
       230                                  240
gcc aag aca aag cca cgg gag gag cag ttc aac agc acg ttc cgt gtg gtc agc gtc ctc  900
 A   K   T   K   P   R   E   E   Q   F   N   S   T   F   R   V   V   S   V   L
       250                                  260
acc gtt gtg cac cag gac tgg ctg aac ggc aag gag tac aag tgc aag gtc tcc aac aaa  960
 T   V   V   H   Q   D   W   L   N   G   K   E   Y   K   C   K   V   S   N   K
       270                                  280
ggc ctc cca gcc tcc atc gag aaa acc atc tcc aaa acc aaa ggg cag ccc cga gaa cca 1020
 G   L   P   A   S   I   E   K   T   I   S   K   T   K   G   Q   P   R   E   P
       290                                  300
cag gtg tac acc ctg ccc cca tcc cgg gag gag atg acc aag aac cag gtc agc ctg acc 1080
 Q   V   Y   T   L   P   P   S   R   E   E   M   T   K   N   Q   V   S   L   T
       310                                  320
tgc ctg gtc aaa ggc ttc tac ccc agc gac atc gcc gtg gag tgg gag agc aat ggg cag 1140
 C   L   V   K   G   F   Y   P   S   D   I   A   V   E   W   E   S   N   G   Q
       330                                  340
ccg gag aac aac tac aag acc aca cct ccc atg ctg gac tcc gac ggc tcc ttc ttc ctc 1200
 P   E   N   N   Y   K   T   T   P   P   M   L   D   S   D   G   S   F   F   L
       350                                  360
tac agc aag ctc acc gtg gac aag agc agg tgg cag cag ggg aac gtc ttc tca tgc tcc 1260
 Y   S   K   L   T   V   D   K   S   R   W   Q   Q   G   N   V   F   S   C   S
       370                                  380
gtg atg cat gag gct ctg cac aac cac tac acg cag aag agc ctc tcc ctg tct ccg ggt 1320
 V   M   H   E   A   L   H   N   H   Y   T   Q   K   S   L   S   L   S   P   G
       390                                  400
aaa tga gaa ttc                                                                  1332
 K       EcoRI
409
```

*FIG 2A*

DNA and deduced amino acid sequences of HuEPO-L-vFc$_{\gamma 4}$

DNA                                          SEQ NO. 19
Amino Acid Sequence                 SEQ NO. 20

```
aag ctt ggc gcg gag atg ggg gtg cac gaa tgt cct gcc tgg ctg tgg ctt ctc ctg tcc   60
HindIII             M   G   V   H   E   C   P   A   W   L   W   L   L   L   S
                   -27                                 -20
ctg ctg tcg ctc cct ctg ggc ctc cca gtc ctg ggc gcc cca cca cgc ctc atc tgt gac  120
 L   L   S   L   P   L   G   L   P   V   L   G   A   P   P   R   L   I   C   D
             -10                                  -1   1
agc cga gtc ctg gag agg tac ctc ttg gag gcc aag gag gcc gag aat atc acg acg ggc  180
 S   R   V   L   E   R   Y   L   L   E   A   K   E   A   E   N   I   T   T   G
     10                                  20
tgt gct gaa cac tgc agc ttg aat gag aat atc act gtc cca gac acc aaa gtt aat ttc  240
 C   A   E   H   C   S   L   N   E   N   I   T   V   P   D   T   K   V   N   F
     30                                  40
tat gcc tgg aag agg atg gag gtc ggg cag cag gcc gta gaa gtc tgg cag ggc ctg gcc  300
 Y   A   W   K   R   M   E   V   G   Q   Q   A   V   E   V   W   Q   G   L   A
     50                                  60
ctg ctg tcg gaa gct gtc ctg cgg ggc cag gcc ctg ttg gtc aac tct tcc cag ccg tgg  360
 L   L   S   E   A   V   L   R   G   Q   A   L   L   V   N   S   S   Q   P   W
     70                                  80
gag ccc ctg cag ctg cat gtg gat aaa gcc gtc agt ggc ctt cgc agc ctc acc act ctg  420
 E   P   L   Q   L   H   V   D   K   A   V   S   G   L   R   S   L   T   T   L
     90                                 100
ctt cgg gct ctg gga gcc cag aag gaa gcc atc tcc cct cca gat gcg gcc tca gct gct  480
 L   R   A   L   G   A   Q   K   E   A   I   S   P   P   D   A   A   S   A   A
    110                                 120
cca ctc cga aca atc act gct gac act ttc cgc aaa ctc ttc cga gtc tac tcc aat ttc  540
 P   L   R   T   I   T   A   D   T   F   R   K   L   F   R   V   Y   S   N   F
    130                                 140
ctc cgg gga aag ctg aag ctg tac aca ggg gag gcc tgc agg aca ggg gac gga tcc ggt  600
 L   R   G   K   L   K   L   Y   T   G   E   A   C   R   T   G   D   G   S   G
    150                                 160
ggc ggt tcc ggt gga ggc gga agc ggc ggt gga gga tca gag tcc aaa tat ggt ccc cca  660
 G   G   S   G   G   G   G   S   G   G   G   G   S   E   S   K   Y   G   P   P
    170                                 180
tgc cca cca tgc cca gca cct gag ttc gcg ggg gga cca tca gtc ttc ctg ttc ccc cca  720
 C   P   P   C   P   A   P   E   F   A   G   G   P   S   V   F   L   F   P   P
    190                                 200
aaa ccc aag gac act ctc atg atc tcc cgg acc cct gag gtc acg tgc gtg gtg gtg gac  780
 K   P   K   D   T   L   M   I   S   R   T   P   E   V   T   C   V   V   V   D
    210                                 220
gtg agc cag gaa gac ccc gag gtc cag ttc aac tgg tac gtg gat ggc gtg gag gtg cat  840
 V   S   Q   E   D   P   E   V   Q   F   N   W   Y   V   D   G   V   E   V   H
    230                                 240
aat gcc aag aca aag ccg cgg gag gag cag ttc aac agc acg tac cgt gtg gtc agc gtc  900
 N   A   K   T   K   P   R   E   E   Q   F   N   S   T   Y   R   V   V   S   V
    250                                 260
ctc acc gtc ctg cac cag gac tgg ctg aac ggc aag gag tac aag tgc aag gtc tcc aac  960
 L   T   V   L   H   Q   D   W   L   N   G   K   E   Y   K   C   K   V   S   N
    270                                 280
aaa ggc ctc ccg tcc tcc atc gag aaa acc atc tcc aaa gcc aaa ggg cag ccc cga gag 1020
 K   G   L   P   S   S   I   E   K   T   I   S   K   A   K   G   Q   P   R   E
    290                                 300
cca cag gtg tac acc ctg ccc cca tcc cag gag gag atg acc aag aac cag gtc agc ctg 1080
 P   Q   V   Y   T   L   P   P   S   Q   E   E   M   T   K   N   Q   V   S   L
    310                                 320
acc tgc ctg gtc aaa ggc ttc tac ccc agc gac atc gcc gtg gag tgg gag agc aat ggg 1140
 T   C   L   V   K   G   F   Y   P   S   D   I   A   V   E   W   E   S   N   G
    330                                 340
cag ccg gag aac aac tac aag acc acg cct ccc gtg ctg gac tcc gac ggc tcc ttc ttc 1200
 Q   P   E   N   N   Y   K   T   T   P   P   V   L   D   S   D   G   S   F   F
    350                                 360
ctc tac agc agg cta acc gtg gac aag agc agg tgg cag gag ggg aat gtc ttc tca tgc 1260
 L   Y   S   R   L   T   V   D   K   S   R   W   Q   E   G   N   V   F   S   C
    370                                 380
tcc gtg atg cat gag gct ctg cac aac cac tac aca cag aag agc ctc tcc ctg tct ctg 1320
 S   V   M   H   E   A   L   H   N   H   Y   T   Q   K   S   L   S   L   S   L
    390                                 400
ggt aaa tga gaa ttc                                                             1335
 G   K       EcoRI
    410
```

*FIG 2B*

DNA and deduced amino acid sequences of HuEPO-L-vFc$_{\gamma 1}$

DNA                           SEQ NO. 21
Amino Acid Sequence           SEQ NO. 22

```
aag ctt ggc gcg gag atg ggg gtg cac gaa tgt cct gcc tgg ctg tgg ctt ctc ctg tcc   60
HindIII          M   G   V   H   E   C   P   A   W   L   W   L   L   L   S
                -27                         -20
ctg ctg tcg ctc cct ctg ggc ctc cca gtc ctg ggc gcc cca cca cgc ctc atc tgt gac  120
 L   L   S   L   P   L   G   L   P   V   L   G   A   P   P   R   L   I   C   D
            -10                              -1   1
agc cga gtc ctg gag agg tac ctc ttg gag gcc aag gag gcc gag aat atc acg acg ggc  180
 S   R   V   L   E   R   Y   L   L   E   A   K   E   A   E   N   I   T   T   G
        10                                  20
tgt gct gaa cac tgc agc ttg aat gag aat atc act gtc cca gac acc aaa gtt aat ttc  240
 C   A   E   H   C   S   L   N   E   N   I   T   V   P   D   T   K   V   N   F
        30                                  40
tat gcc tgg aag agg atg gag gtc ggg cag cag gcc gta gaa gtc tgg cag ggc ctg gcc  300
 Y   A   W   K   R   M   E   V   G   Q   Q   A   V   E   V   W   Q   G   L   A
        50                                  60
ctg ctg tcg gaa gct gtc ctg cgg ggc cag gcc ctg ttg gtc aac tct tcc cag ccg tgg  360
 L   L   S   E   A   V   L   R   G   Q   A   L   L   V   N   S   S   Q   P   W
        70                                  80
gag ccc ctg cag ctg cat gtg gat aaa gcc gtc agt ggc ctt cgc agc ctc acc act ctg  420
 E   P   L   Q   L   H   V   D   K   A   V   S   G   L   R   S   L   T   T   L
        90                                  100
ctt cgg gct ctg gga gcc cag aag gaa gcc atc tcc cct cca gat gcg gcc tca gct gct  480
 L   R   A   L   G   A   Q   K   E   A   I   S   P   P   D   A   A   S   A   A
        110                                 120
cca ctc cga aca atc act gct gac act ttc cgc aaa ctc ttc cga gtc tac tcc aat ttc  540
 P   L   R   T   I   T   A   D   T   F   R   K   L   F   R   V   Y   S   N   F
        130                                 140
ctc cgg gga aag ctg aag ctg tac aca ggg gag gcc tgc agg aca ggg gac gga tcc ggt  600
 L   R   G   K   L   K   L   Y   T   G   E   A   C   R   T   G   D   G   S   G
        150                                 160
ggc ggt tcc ggt gga ggc gga agc ggc ggt gga gga tca gac aaa act cac aca tgc cca  660
 G   G   S   G   G   G   G   S   G   G   G   G   S   D   K   T   H   T   C   P
        170                                 180
ccg tgc cca gca cct gaa gtc gcg ggg gga ccg tca gtc ttc ctc ttc ccc cca aaa ccc  720
 P   C   P   A   P   E   V   A   G   G   P   S   V   F   L   F   P   P   K   P
        190                                 200
aag gac acc ctc atg atc tcc cgg aca cct gag gtc aca tgc gtg gtg gtg gac gtg agc  780
 K   D   T   L   M   I   S   R   T   P   E   V   T   C   V   V   V   D   V   S
        210                                 220
cac gaa gac cct gag gtc aag ttc aac tgg tac gtg gac ggc gtg gag gtg cat aat gcc  840
 H   E   D   P   E   V   K   F   N   W   Y   V   D   G   V   E   V   H   N   A
        230                                 240
aag aca aag ccg cgg gag gag cag tac aac agc acg tac cgg gtg gtc agc gtc ctc acc  900
 K   T   K   P   R   E   E   Q   Y   N   S   T   Y   R   V   V   S   V   L   T
        250                                 260
gtc ctg cac cag gac tgg ctg aat ggc aag gag tac aag tgc aag gtc tcc aac aaa gcc  960
 V   L   H   Q   D   W   L   N   G   K   E   Y   K   C   K   V   S   N   K   A
        270                                 280
ctc cca gcc tcc atc gag aaa acc atc tcc aaa gcc aaa ggg cag ccc cga gaa cca cag 1020
 L   P   A   S   I   E   K   T   I   S   K   A   K   G   Q   P   R   E   P   Q
        290                                 300
gtg tac acc ctg ccc cca tcc cgg gat gag ctg acc aag aac cag gtc agc ctg acc tgc 1080
 V   Y   T   L   P   P   S   R   D   E   L   T   K   N   Q   V   S   L   T   C
        310                                 320
ctg gtc aaa ggc ttc tat ccc agc gac atc gcc gtg gag tgg gag agc aat ggg cag ccg 1140
 L   V   K   G   F   Y   P   S   D   I   A   V   E   W   E   S   N   G   Q   P
        330                                 340
gag aac aac tac aag acc acg cct ccc gtg ctg gac tcc gac ggc tcc ttc ttc ctc tac 1200
 E   N   N   Y   K   T   T   P   P   V   L   D   S   D   G   S   F   F   L   Y
        350                                 360
agc aag ctc acc gtg gac aag agc agg tgg cag cag ggg aac gtc ttc tca tgc tcc gtg 1260
 S   K   L   T   V   D   K   S   R   W   Q   Q   G   N   V   F   S   C   S   V
        370                                 380
atg cat gag gct ctg cac aac cac tac acg cag aag agc ctc tcc ctg tct ccg ggt aaa 1320
 M   H   E   A   L   H   N   H   Y   T   Q   K   S   L   S   L   S   P   G   K
        390                                 400
tga gaa ttc                                                                      1329
    EcoRI
```

FIG 2C

Amino acid sequence in some peptide linkers

SEQ ID NO:23
GlySerGlyGlyGlySerGlyGlyGlyGlySerGlyGlyGlyGlySer

SEQ ID NO:24
GluProLysSerCysAspLysThrHisThrCysProProCysPro

SEQ ID NO:25
AspLysThrHisThrCysProProCysPro

SEQ ID NO:29
GlyGlyGlyGlySer

*FIG 3*

FC FUSION PROTEINS OF HUMAN ERYTHROPOIETIN WITH INCREASED BIOLOGICAL ACTIVITIES

BACKGROUND

Erythropoietin (EPO) is a 30.4 kilodalton (kDa) glycoprotein hormone that promotes the proliferation of erythroid progenitor cells and supports their differentiation into mature erythrocytes (see, for example, Krantz, *Blood*, 77:419-434, 1991). EPO is produced in the adult kidney and the fetal liver. In adults, EPO is produced primarily in kidney cells in response to hypoxia or anemia and circulates in the bloodstream. EPO targets the 66 kDa specific receptor (EPO-Rc) found almost exclusively on the surface of erythroid progenitor cells present in bone marrow. Upon binding EPO, the receptor is activated and undergoes homodimerization, followed by tyrosine phosphorylation. Subsequently, a series of intracellular signal transduction events take place, leading to the increase of the number of the progenitor cells and their maturation into erythrocytes (see, for example, Lodish et al., *Cold Spring Harbor Symp. Quant. Biol.*, 60:93-104, 1995).

Recombinant human EPO (rHuEPO) is widely used in the treatment of patients with chronic anemia due to renal diseases at both end-stage and pre-dialysis phases. Administration of EPO has also been successful to treat anemia in patients caused by cancer chemotherapy, rheumatoid arthritis, AZT treatment for HIV infection and myelodysplastic syndrome. No direct toxic effect of treatment has been reported and the benefits of blood transfusion could be achieved without the transfusion.

The concentration of EPO in normal human serum varies approximately from 0.01 to 0.03 units/ml. Supplemental EPO is a desirable treatment in cases of renal failure with decreased EPO production. The half-life for the serum clearance of intravenous (i.v.) rHuEPO is approximately 4 to 13 h. The peak serum concentration for subcutaneous (s.c.) rHuEPO occurs in 5 to 24 h after injection with an elimination half-life of 17 h. The s.c. administration route can therefore lead to much longer retention in the blood than i.v. administration of the same dose. The mechanism responsible for clearing EPO from the serum remains unclear. In animal experiments, less than 5% is excreted by the kidney. The liver, which rapidly removes asialated EPO, has not been shown to play a significant role in clearing EPO (see, for example, Fried, *Annu. Rev. Nutr.*, 15:353-377, 1995).

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and soluble receptors (see, for example, Capon et al., *Nature*, 337:525-531, 1989; Chamow et al., *Trends Biotechnol.*, 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the CH1 domains and light chains. Due to the structural homology, Fc fusion proteins exhibit in vivo pharmacokinetic profile comparable to that of human IgG with a similar isotype. This approach has been applied to several therapeutically important cytokines, such as IL-2 and IFN-$\alpha_{2a}$, and soluble receptors, such as TNF-Rc and IL-5-Rc (see, for example, U.S. Pat. Nos. 5,349,053 and 6,224,867). To extend the circulating half-life of EPO and/or to increase its biological activity, it is desirable to make fusion proteins containing EPO linked to the Fc portion of the human IgG protein as disclosed or described in this invention.

In most of the reported Fc fusion protein molecules, a hinge region serves as a spacer between the Fc region and the cytokine or soluble receptor at the amino-terminus, allowing these two parts of the molecule to function separately (see, for example, Ashkenazi et al., *Current Opinion in Immunology*, 9:195-200, 1997). Relative to the EPO monomer, a fusion protein consisting of two complete EPO domains separated by a 3- to 7-amino acid peptide linker exhibited reduced activity (Qiu et al., *J. Biol. Chem.*, 273: 11173-11176, 1998). However, when the peptide linker between the two EPO domains was 17 amino acids in length, the dimeric EPO molecule exhibited considerably enhanced in vitro and in vivo activities. The enhanced activity has been shown to be due to an increased in vitro activity coupled with a different pharmacokinetic profile in mice (see, for example, Sytkowski et al., *J. Biol. Chem.*, 274: 24773-24778, 1999; U.S. Pat. No. 6,187,564). A human EPO fusion protein with an appropriate peptide linker between the HuEPO and Fc moieties (HuEPO-L-Fc) is more active than rHuEPO, with in vitro activity at least 2-fold as that of rHuEPO on a molar basis. It is discovered according to this invention that an added peptide linker present between HuEPO and a human IgG Fc variant enhances the in vitro biological activity of the HuEPO-L-Fc molecule in two ways: (1) keeping the Fc region away from the EPO-Rc binding sites on EPO, and (2) keeping one EPO from the other EPO domain, so both EPO domains can interact with EPO-Rc on the erythroid progenitor cells independently. For the present invention, a flexible peptide linker of about 20 or fewer amino acids in length is preferred. It is preferably to use a peptide linker comprising of two or more of the following amino acids: glycine, serine, alanine, and threonine.

The Fc region of human immunoglobulins plays a significant role in immune defense for the elimination of pathogens. Effector functions of IgG are mediated by the Fc region through two major mechanisms: (1) binding to the cell surface Fc receptors (Fc$_\gamma$Rs) can lead to ingestion of pathogens by phagocytosis or lysis by killer cells via the antibody-dependent cellular cytotoxicity (ADCC) pathway, or (2) binding to the C1q part of the first complement component C1 initiates the complement-dependent cytotoxicity (CDC) pathway, resulting in the lysis of pathogens. Among the four human IgG isotypes, IgG1 and IgG3 are effective in binding to Fc$_\gamma$R. The binding affinity of IgG4 to Fc$_\gamma$R is an order of magnitude lower than that of IgG1 or IgG3, while binding of IgG2 to Fc$_\gamma$R is below detection. Human IgG1 and IgG3 are also effective in binding to C1q and activating the complement cascade. Human IgG2 fixes complement poorly, and IgG4 appears quite deficient in the ability to activate the complement cascade (see, for example, Jefferis et al., *Immunol. Rev.*, 163:59-76, 1998). For therapeutic use in humans, it is essential that when HuEPO-L-Fc binds to EPO-Rc on the surface of the erythroid progenitor cells, the Fc region of the fusion protein will not mediate undesirable effector functions, leading to the lysis or removal of these progenitor cells. Accordingly, the Fc region of HuEPO-L-Fc must be of a non-lytic nature, i.e. the Fc region must be inert in terms of binding to Fc$_\gamma$Rs and C1q for the triggering of effector functions. It is clear that none of the naturally occurring IgG isotypes is suitable for use to produce the HuEPO-L-Fc fusion protein. To obtain a non-lytic Fc, certain amino acids of the natural Fc region have to be mutated for the attenuation of the effector functions.

By comparing amino acid sequences of human and murine IgG isotypes, a portion of Fc near the N-terminal end of the CH2 domain is implicated to play a role in the binding of IgG Fc to $Fc_\gamma Rs$. The importance of a motif at positions 234 to 237 has been demonstrated using genetically engineered antibodies (see, for example, Duncan et al., *Nature*, 332:563-564, 1988). The numbering of the amino acid residues is according to the EU index as described in Kabat et al. (in *Sequences of Proteins of Immunological Interest*, 5$^{th}$ Edition, United States Department of Health and Human Services, 1991). Among the four human IgG isotypes, IgG1 and IgG3 bind $Fc_\gamma Rs$ the best and share the sequence Leu234-Leu-Gly-Gly237 (only IgG1 is shown in FIG. 1). In IgG4, which binds $Fc_\gamma Rs$ with a lower affinity, this sequence contains a single amino acid substitution, Phe for Leu at position 234. In IgG2, which does not bind $Fc_\gamma Rs$, there are two substitutions and a deletion leading to Val234-Ala-Gly237 (FIG. 1). To minimize the binding of Fc to $Fc_\gamma R$ and hence the ADCC activity, Leu235 in IgG4 has been replaced by Ala (see, for example, Hutchins et al., *Proc. Natl. Acad. Sci. USA*, 92:11980-11984, 1995). IgG1 has been altered in this motif by replacing Glu233-Leu-Leu235 with Pro233-Val-Ala235, which is the sequence from IgG2. This substitution resulted in an IgG1 variant devoid of $Fc_\gamma R$-mediated ability to deplete target cells in mice (see, for example, Isaacs et al., *J. Immunol.*, 161:3862-3869, 1998).

A second portion that appears to be important for both $Fc_\gamma R$ and C1q binding is located near the carboxyl-terminal end of CH2 domain of human IgG (see, for example, Duncan et al., *Nature*, 332:738-740, 1988). Among the four human IgG isotypes, there is only one site within this portion that shows substitutions: Ser330 and Ser331 in IgG4 replacing Ala330 and Pro331 present in IgG1, IgG2, and IgG3 (FIG. 1). The presence of Ser330 does not affect the binding to $Fc_\gamma R$ or C1q. The replacement of Pro331 in IgG1 by Ser virtually abolished IgG1 ability to C1q binding, while the replacement of Ser331 by Pro partially restored the complement fixation activity of IgG4 (see, for example, Tao et al., *J. Exp. Med.*, 178:661-667, 1993; Xu et al., *J. Biol. Chem.*, 269:3469-3474, 1994).

We discover that at least three Fc variants (vFc) can be designed for the production of HuEPO-L-vFc fusion proteins (FIG. 1). Human IgG2 Fc does not bind $Fc_\gamma R$ but showed weak complement activity. An $Fc_{\gamma 2}$ variant with Pro331Ser mutation should have less complement activity than natural $Fc_{\gamma 2}$ while remain as a non-binder to $Fc_\gamma R$. IgG4 Fc is deficient in activating the complement cascade, and its binding affinity to $Fc_\gamma R$ is about an order of magnitude lower than that of the most active isotype, IgG1. An $Fc_{\gamma 4}$ variant with Leu235Ala mutation should exhibit minimal effector functions as compared to the natural $Fc_{\gamma 4}$. The $Fc_{\gamma 1}$ variant with Leu234Val, Leu235Ala and Pro331Ser mutations also will exhibit much less effector functions than the natural $Fc_{\gamma 1}$. These Fc variants are more suitable for the preparation of the EPO fusion proteins than naturally occurring human IgG Fc. It is possible that other replacements can be introduced for the preparation of a non-lytic Fc without compromising the circulating half-life or causing any undesirable conformational changes.

There are many advantages with the present invention. The increased activity and prolonged presence of the HuEPO-L-vFc fusion protein in the serum can lead to lower dosages as well as less frequent injections. Less fluctuations of the drug in serum concentrations also means improved safety and tolerability. Less frequent injections may result in better patient compliance and quality of life. The HuEPO-L-vFc fusion protein containing a non-lytic Fc variant will therefore contribute significantly to the management of anemia caused by conditions including renal failure, cancer chemotherapy, rheumatoid arthritis, AZT treatment for HIV infection, and myelodysplastic syndrome.

SUMMARY OF THE INVENTION

One aspect of the present invention relates to a HuEPO-L-vFc fusion protein. The HuEPO-L-vFc fusion protein comprises HuEPO, a peptide linker, and a human IgG Fc variant. It is preferably to use a flexible peptide linker of 20 or fewer amino acids in length which comprises of two or more of the following amino acids: glycine, serine, alanine, and threonine. The IgG Fc variant is of non-lytic nature and contains amino acid mutations as compared to naturally occurring IgG Fc.

It is another embodiment of the present invention that the human Ig Fc comprises a hinge, CH2, and CH3 domains of human IgG, such as human IgG1, IgG2, and IgG4. The CH2 domain contains amino acid mutations at positions 228, 234, 235, and 331 (defined by the EU numbering system) to attenuate the effector functions of Fc.

In yet another embodiment of the present invention, a method is disclosed to make or produce such fusion proteins from a mammalian cell line such as a CHO-derived cell line. Growing transfected cell lines under conditions such that the recombinant fusion protein is expressed in its growth medium in excess of 10, preferably 30, μg per million cells in a 24 hour period. These HuEPO-L-vFc fusion proteins exhibit increased biological activity and extended serum half-life without undesirable side effects, leading to improved pharmacokinetics and pharmacodynamics, thus lower dosages and fewer injections would be needed to achieve similar efficacies.

BRIEF DESCRIPTIONS OF THE DRAWINGS

FIG. 1 shows the amino acid sequence alignment from the hinge and CH2 regions of human IgG1, IgG2, IgG4 and their variants. Three portions are compared: amino acid position 228, 234-237, and 330-331. Amino acid mutations of the variants are indicated in bold italics. The EU numbering system is used for the amino acid residues.

FIG. 2 shows the nucleotide sequence and deduced amino acid sequence of (A) HuEPO-L-vFc$_{\gamma 2}$, (B) HuEPO-L-vFc$_{\gamma 4}$, and (C) HuEPO-L-vFc$_{\gamma 1}$ as the HindIII-EcoRI fragment in the respective pEFP expression vector. The peptide from amino acid residues −27 to −1 is the leader peptide of human EPO. The mature protein contains human EPO (amino acid residues 1 to 165), a peptide linker (amino acid residues 166 to 181), and a Fc variant (amino acid residues 182 to 409 of vFc$_{\gamma 2}$, 182 to 410 of vFc$_{\gamma 4}$, and 182 to 408 of vFc$_{\gamma 1}$). In the Fc regions, nucleotide and corresponding amino acid mutations in bold are also underlined. FIG. 3 shows non-limiting examples of amino acid sequences (16, 15, 10, and 4 amino acids) in the flexible peptide linkers and an example.

DETAILED DESCRIPTION OF THE INVENTION

1. Construction of the Gene Encoding the HuEPO-L-vFc$_{\gamma 2}$ Fusion Protein A fusion protein is assembled from several DNA segments. To obtain the gene encoding the leader peptide and mature protein of human EPO, cDNA library of human fetal liver or kidney (obtained from Invitrogen, Carlsbad, Calif.)

is used as the template in polymerase chain reaction (PCR). For the convenience of cloning, SEQ ID NO:1 (Table 1), which incorporates a restriction enzyme cleavage site (HindIII) is used as the 5' oligonucleotide primer. Table 1 shows the sequences of oligonucleotides used for the cloning of the HuEPO-L-vFc fusion proteins. The 3' primer (SEQ ID NO:2) eliminates the EPO termination codon and incorporates a BamHI site. The resulting DNA fragments of approximately 600 bp in length are inserted into a holding vector such as pUC19 at the HindIII and BamHI sites to give the pEPO plasmid. The sequence of the human EPO gene is confirmed by DNA sequencing.

The gene encoding the Fc region of human IgG2 ($Fc_{\gamma2}$) is obtained by reverse transcription and PCR using RNA prepared from human leukocytes and appropriate 5' (SEQ ID NO:3) and 3' (SEQ ID NO:4) primers. Resulting DNA fragments of $Fc_{\gamma2}$ containing complete sequences of the hinge, CH2, and CH3 domains of IgG2 will be used as the template to generate the $Fc_{\gamma2}$ Pro331Ser variant ($vFc_{\gamma2}$) in which Pro at position 331 of $Fc_{\gamma2}$ is replaced with Ser. To incorporate this mutation, two segments are produced and then assembled by using the natural $Fc_{\gamma2}$ as the template in overlapping PCR. The 5' segment is generated by using SEQ ID NO:3 as the 5' primer and SEQ ID NO:5 as the 3' primer. The 3' segment is generated by using SEQ ID NO:6 as the 5' primer and SEQ ID NO:4 as the 3' primer. These two segments are then joined at the region covering the Pro331 Ser mutation by using SEQ ID NO:7 as the 5' primer and SEQ ID NO:4 as the 3' primer. The SEQ ID NO:7 primer contains sequences encoding a 16-amino acid Gly-Ser peptide linker including a BamHI restriction enzyme site. The resulting DNA fragments of approximately 700 bp in length are inserted into a holding vector such as pUC19 at the BamHI and EcoRI sites to give the pL-$vFc_{\gamma2}$ plasmid. The sequence of the gene is confirmed by DNA sequencing.

To prepare the HuEPO-L-$vFc_{\gamma2}$ fusion gene, the EPO fragment is excised from the pEPO plasmid with HindIII and BamHI and is purified by agarose gel electrophoresis. The purified fragment is then inserted to the 5'-end of the peptide linker in the pL-$vFc_{\gamma2}$ plasmid to give the pEPO-L-$vFc\gamma2$ plasmid. The fusion gene comprises HuEPO, a Gly-Ser peptide linker and the $Fc_{\gamma2}$ variant gene.

The presence of a peptide linker between the EPO and Fc moieties increases the flexibility of the EPO domains and enhances its biological activity (see, for example, Sytkowski et al., *J. Biol. Chem.*, 274:24773-8, 1999). For the present invention, a peptide linker of about 20 or fewer amino acids in length is preferred. Peptide linker comprising two or more of the following amino acids: glycine, serine, alanine, and threonine can be used. An example of the peptide linker contains Gly-Ser peptide building blocks, such as GlyGlyGlyGlySer (SEQ ID NO. 29). FIG. 2A shows a fusion gene (SEQ ID NO. 17) containing sequences encoding HuEPO, a 16-amino acid peptide linker (GlySerGlyGlyGlySerGlyGlyGlyGlySerGlyGlyGlyGlySer, SEQ ID NO: 23), and the $Fc_{\gamma2}$ Pro331Ser variant, and its corresponding amino acid sequence (SEQ ID NO. 18).

The complete gene encoding the HuEPO-L-vFc fusion protein is then inserted at the HindIII and EcoRI sites of a mammalian expression vector, such as pcDNA3 (Invitrogen). The final expression vector plasmid, named pEFP2, contains the cytomegalovirus early gene promoter-enhancer which is required for high level expression in mammalian cells. The plasmid also contains selectable markers to confer ampicillin resistance in bacteria, and G418 resistance in mammalian cells. In addition, the pEFP2 expression vector contains the dihydrofolate reductase (DHFR) gene to enable the co-amplification of the HuEPO-L-vFcγ2 fusion gene and the DHFR gene in the presence of methotrexate (MTX) when the host cells are deficient in the DHFR gene expression (see, for example, U.S. Pat. No. 4,399,216).

2. Construction of the Gene Encoding the HuEPO-L-vFc Fusion Protein

Human IgG4 is observed partly as half antibody molecules due to the dissociation of the inter-heavy chain disulfide bonds in the hinge domain. This is not seen in the other three human IgG isotypes. A single amino acid substitution replacing Ser228 with Pro, which is the residue found at this position in IgG1 and IgG2, leads to the formation of IgG4 complete antibody molecules (see, for example, Angal et al., *Molec. Immunol.*, 30:105-108, 1993; Owens et al., *Immunotechnology*, 3:107-116, 1997; U.S. Pat. No. 6,204,007). The $Fc_{\gamma4}$ variant containing Leu235Ala mutation for the minimization of FcR binding will also give rise to a homogeneous fusion protein preparation with this additional Ser228Pro mutation.

The gene encoding the Fc region of human IgG4 ($Fc_{\gamma4}$) is obtained by reverse transcription and PCR using RNA prepared from human leukocytes and appropriate 5' primer (SEQ ID NO:8) and 3' primer (SEQ ID NO:9). Resulting DNA fragments of $Fc_{\gamma4}$ containing complete sequences of the hinge, CH2, and CH3 domains of IgG4 is used as the template to generate the $Fc_{\gamma4}$ variant with Ser228Pro and Leu235Ala mutations ($vFc_{\gamma4}$) in which Ser228 and Leu235 have been replaced with Pro and Ala, respectively. The CH2 and CH3 domains are amplified using the 3' primer (SEQ ID NO:9) and a 5' primer containing the Leu235Ala mutation (SEQ ID NO:10). This amplified fragment, together with a synthetic oligonucleotide of 60 bases in length (SEQ ID NO:11) containing both Ser228Pro and Leu235Ala mutations, are joined in PCR by using SEQ ID NO:12 as the 5' primer and SEQ ID NO:9 as the 3' primer. The SEQ ID NO:12 primer contains sequences encoding a 16-amino acid Gly-Ser peptide linker including the BamHI site. The resulting DNA fragments of approximately 700 bp in length are inserted into a holding vector such as pUC19 at the BamHI and EcoRI sites to give the pL-vFcγ4 plasmid. The sequence of the gene is confirmed by DNA sequencing.

To prepare the HuEPO-L-$vFc_{\gamma4}$ fusion gene, the HuEPO fragment is excised from the pEPO plasmid with HindIII and BamHI and then inserted to the 5'-end of the peptide linker in the pL-vFcγ4 plasmid to give the pEPO-L-vFcγ4 plasmid. This fusion gene comprising HuEPO, a 16-amino acid Gly-Ser peptide linker and the $Fc_{\gamma4}$ variant gene is then inserted at the HindIII and EcoRI sites of a mammalian expression vector, such as pcDNA3 (Invitrogen), as described for the HuEPO-L-$Fc_{\gamma2}$ fusion protein. The final expression vector plasmid is designated as pEFP4. FIG. 2B shows a fusion gene (SEQ ID NO. 19) containing sequences encoding HuEPO, a 16-amino acid peptide linker (GlySerGlyGlyGlySerGlyGlyGlyGlySerGlyGlyGlyGlySer, SEQ ID NO: 23), and the $Fc_{\gamma4}$ variant with Ser228Pro and Leu235Ala mutations, and its corresponding amino acid sequence (SEQ ID NO. 20).

3. Construction of the Gene Encoding the HuEPO-L-$vFc_{\gamma1}$ Fusion Protein

The hinge domain of human IgG1 heavy chain contains 15 amino acid residues (GluProLysSerCysAspLysThrHisThrCysProProCysPro), SEQ ID NO: 24 including 3 cysteine residues. Out of these 3 cysteine residues, the 2nd and 3rd are involved in the formation of disulfide bonding between two heavy chains. The 1st cysteine residue is involved in the disulfide bonding to the light chain of IgG.

Since there is no light chain present in the Fc fusion protein molecule, this cysteine residue may pair with other cysteine residues, leading to nonspecific disulfide bonding. The hinge domain of $Fc_{\gamma 1}$ can be truncated to eliminate the 1st cysteine residue (AspLysThrHisThrCysProProCysPro), SEQ ID NO: 25. The gene encoding the $Fc_{\gamma 1}$ region is obtained by reverse transcription and PCR using RNA prepared from human leukocytes and appropriate 5' primer (SEQ ID NO:13) and 3' primer (SEQ ID NO:4). Resulting DNA fragments containing the truncated hinge and complete sequences of CH2 and CH3 domains of $Fc_{\gamma 1}$ is used as the template to generate the $Fc_{\gamma 1}$ variant with Leu234Val, Leu235Ala, and Pro331 Ser mutations ($vFc_{\gamma 1}$).

One way to incorporate these mutations is as follows: two segments are produced and then assembled by using the natural $Fc_{\gamma 1}$ as the template in overlapping PCR. The 5' segment is generated by using SEQ ID NO:14 as the 5' primer and SEQ ID NO:5 as the 3' primer. This 5' primer contains the Leu234Val, Leu235Ala mutations and the 3' primer contains the Pro331Ser mutation. The 3' segment is generated by using SEQ ID NO:6 as the 5' primer and SEQ ID NO:4 as the 3' primer. These 5' and 3' segments are then joined at the region covering the Pro331 Ser mutation by using SEQ ID NO:14 as the 5' primer and SEQ ID NO:4 as the 3' primer. This amplified fragment of approximately 650 bp in length, together with a synthetic oligonucleotide of 55 bases (SEQ ID NO:15) containing Leu234Val and Leu235Ala, are joined in PCR by using SEQ ID NO:16 as the 5' primer and SEQ ID NO:4 as the 3' primer. The SEQ ID NO:16 primer contains sequences encoding a 16-amino acid Gly-Ser peptide linker including the BamHI site. The resulting DNA fragments of approximately 700 bp in length are inserted into a holding vector such as pUC19 at the BamHI and EcoRI sites to give the pL-vFcγ1 plasmid. The sequence of the gene is confirmed by DNA sequencing.

To prepare the HuEPO-L-$vFc_{\gamma 1}$ fusion gene, the EPO fragment is excised from the pEPO plasmid with HindIII and BamHI and inserted to the 5'-end of the peptide linker in the pL-vFcγ1 plasmid to give the pEPO-L-vFcγ1 plasmid. The fusion gene comprising HuEPO, a 16-amino acid Gly-Ser peptide linker, and the $Fc_{\gamma 1}$ variant gene is then inserted at the HindIII and EcoRI sites of a mammalian expression vector, such as pcDNA3 (Invitrogen), as described for the HuEPO-L-$vFc_{\gamma 2}$ fusion protein. The final expression vector plasmid is designated as pEFP1. FIG. 2C shows a fusion gene (SEQ ID NO. 21) containing sequences encoding HuEPO, a 16-amino acid peptide linker (GlySerGlyGlyGly-SerGlyGlyGlyGlySerGlyGlyGlyGlySer, SEQ ID NO: 23), and the $Fc_{\gamma 1}$ variant with Leu234Val, Leu235Ala and Pro331Ser mutations, and its corresponding amino acid sequence (SEQ ID NO. 22).

4. Expression of the Fusion Protein in Transfected Cell Lines

The recombinant pEFP1, pEFP2 or pEFP4 expression vector plasmid is transfected into a mammalian host cell line to achieve the expression of the HuEPO-L-vFc fusion protein. For stable high levels of expression, a preferred host cell line is Chinese Hamster Ovary (CHO) cells deficient in the DHFR enzyme (see, for example, U.S. Pat. No. 4,818, 679). A preferred method of transfection is electroporation. Other methods, including calcium phosphate co-precipitation, lipofectin, and protoplast fusion, can also be used. For electroporation, 10 μg of plasmid DNA linearized with BspCI is added to 2 to $5 \times 10^7$ cells in a cuvette using Gene Pulser Electroporator (Bio-Rad Laboratories, Hercules, Calif.) set at an electric field of 250 V and a capacitance of 960 μFd. Two days following the transfection, the media are replaced with growth media containing 0.8 mg/ml of G418. Transfectants resistant to the selection drug are tested for the secretion of the fusion protein by anti-human IgG Fc ELISA. Quantitation of the expressed fusion protein can also be carried out by ELISA using anti-HuEPO assays. The wells producing high levels of the Fc fusion protein are subcloned by limiting dilutions on 96-well tissue culture plates.

To achieve higher levels of the fusion protein expression, co-amplification is preferred by utilizing the gene of DHFR which can be inhibited by the MTX drug. In growth media containing increasing concentrations of MTX, the transfected fusion protein gene is co-amplified with the DHFR gene. Transfectants capable of growing in media with up to 1 μg/ml of MTX are again subcloned by limiting dilutions. The subcloned cell lines are further analyzed by measuring the secretion rates. Several cell lines yielding secretion rate levels over about 10, preferably about 30 μg/$10^6$ cells/24 h, are adapted to suspension culture using serum-free growth media. The conditioned media are then used for the purification of the fusion protein.

Sugar side chain structures are crucial for the in vivo activity of EPO. The terminal sugar chain of the Asn-linked carbohydrate contains sialic acids, repeating poly-N-acetyl-lactosamine and galactose. Recombinant HuEPO expressed in certain mammalian cells such as NS0 is known to give proteins with low sialic acid content. Removal of sialic acids, which leads to exposure of the penultimate galactose residues, increases the affinity for hepatic asialoglycoprotein binding lectin. This trapping pathway results in decrease of in vivo biological activity as measured in whole animals. Recombinant HuEPO produced in CHO cells exhibit glycosylation patterns very similar to that found in the natural EPO (see, for example, Takeuchi et al., *Proc. Natl. Acad. Sci. USA*, 86:7819-22, 1989). The HuEPO-L-vFc fusion proteins expressed and produced in accordance with this invention will show enhanced biological activities when compared to rHuEPO on a molar basis.

5. Purification and Characterization of the Fusion Protein

Conditioned media containing the fusion protein are titrated with 1 N NaOH to a pH of 7 to 8 and filtered through a 0.45 micron cellulose nitrate filter. The filtrate is loaded onto a Prosep A column equilibrated in phospate-buffered saline (PBS). After binding of the fusion protein to Prosep A, the flow-through fractions are discarded. The column is washed with PBS until OD at 280 nm is below 0.01. The bound fusion protein is then eluted with 0.1 M citrate buffer at pH 3.75. After neutralizing with 0.4 volume of 1 M $K_2HPO_4$, fractions containing purified protein are pooled and dialyzed against PBS. The solution is then filtered through a 0.22 micron cellulose nitrate filter and stored at 4° C. The molecular weight of purified HuEPO-L-vFc protein is in the range of 110 and 130 kDa by SDS-PAGE under non-reducing conditions. Under reducing conditions, the purified protein migrates around approximately 60 kDa. The fusion protein is quantitated by BCA protein assay using BSA as the standard.

6. In Vitro Biological Assays

Supernatants of transfectants or purified proteins can be tested for their ability to stimulate the proliferation of TF-1 cells (Kitamura et al., *J. Cell. Physiol.*, 140:323-334, 1989). TF-1 cells naturally express human EPO-Rc on their cell surface and are responsive to EPO. The cells are maintained in growth medium (RPMI-1640 medium containing 10% FCS and human IL-5 at 1 to 5 ng/ml). Log phase TF-1 cells are collected and washed with assay medium (growth medium without human IL-5). A total of $1 \times 10^4$ cells per sample of TF-1 in 50 µl is added to each well of a 96-well tissue culture plate. The cells are incubated with 50 µl of assay media containing various concentrations of the HuEPO-L-vFc fusion protein or the rHuEPO control from 0.01 to 100 nM each. The plate is kept at 37° C. and 5% $CO_2$ in a humidified incubator for 4 days before 10 µl of MTT (2.5 mg/ml in PBS) is added to each well. After 4 h, the cells and formazan are solubilized by adding 100 µl per well of 10% SDS in 0.01 N HCl. The plate is then read at 550 nm with the reference beam set at 690 nm. The OD reading is plotted against the concentration of rHuEPO or the fusion protein. The inflection point of the sigmoidal curve represents the concentration at which 50% of the maximal effect, ED50, is induced. The biological activity of HuEPO-L-vFc relative to that of rHuEPO can therefore be compared quantitatively. Preferably, the fusion proteins should exhibit an enhanced activity of at least 2 fold relative to that of rHuEPO on a molar basis. In one embodiment of the present invention, the specific activity of the HuEPO-L-vFc fusion protein is in the range of about 6 to about $8\times10^6$ units/µmole, compared to about 3 to about $4\times10^6$ units/µmole for rHuEPO.

Supernatants of transfectants or purified proteins can also be tested for their ability to stimulate the proliferation and differentiation of human bone marrow progenitor cells to form red blood cell colonies, colony forming unit-erythroid (CFU-E). The procedure is as follows. Light-density cells from human bone marrow centrifuged over Ficoll-Pague are washed and resuspended at $1\times10^6$ cells/ml in Iscove's modified Dulbecco's medium (IMDM) containing 5% FCS. These cells are incubated in a tissue culture dish overnight at 37° C. and 5% $CO_2$ to remove all adherent cells including monocytes, macrophages, endothelial cell, and fibroblasts. Cells in suspension are then adjusted to $1\times10^5$ cells/ml in IMDM containing 5% FCS. For the assay, 0.3 ml of cells, 15 µl of stem cell factor at 20 µg/ml, 2.4 ml of methylcellulose, and 0.3 ml of media containing several concentrations of HuEPO-L-vFc (or rHuEPO control) are mixed. One ml of this cell mixture is plated on a 35-mm petri dish. The dishes are then kept at 37° C. and 5% $CO_2$ for 10 to 14 d before the colonies are counted. A dose responsive curve can be plotted against the concentrations of HuEPO-L-vFc relative to those of rHuEPO.

7. In Vivo Pharmacokinetic Studies in Rats

Fisher rats (Harlan Bioproducts for Science, Indianapolis, Ind.) with an average body weight of about 500 g are injected i.v. through the tail vein or s.c. with 100 units of rHuEPO or the HuEPO-L-vFc fusion protein. An equal volume of PBS is injected as a control. Serial 0.5-ml samples are taken through retro-orbital bleeds at different points (0, 0.2, 1, 4, 24, 48, 96, and 168 h) after injection. There are 3 rats for each time point. Whole blood is collected into tubes containing anticoagulant, cells are removed, and plasma is frozen at $-70°$ C. until assay is carried out.

Serum samples are used for TF-1 cell assays, which measure the activity of EPO-mediated cell proliferation. A total of $1\times10^4$ cells per sample of TF-1 in 50 µl is added to each well of a 96-well tissue culture plate. The cells are incubated with 50 µl of assay media containing various concentrations of titrated blood samples. The plate is kept at 37° C. and 5% $CO_2$ in a humidified incubator for 4 days. Viable cells are stained with 10 µl of MTT (2.5 mg/ml in PBS). After 4 h, the cells and formazan are solubilized by adding 100 µl per well of 10% SDS in 0.01 N HCl. The plate is then read at 550 nm with the reference beam set at 690 nm. The activities of serum samples are plotted against time points for the calculation of the circulation time. The activity of HuEPO-L-vFc decreases much slower than that of the rHuEPO control, indicating the longer circulating half-life of the fusion protein in rats.

The examples described above are for illustration purposes only. They are not intended and should not be interpreted to limit either the scope or the spirit of this invention. It can be appreciated by those skilled in the art that many other variations or substitutes can be used as equivalents for the purposes of this invention, which is defined solely by the written description and the following claims.

TABLE 1

Sequences of Oligonucleotides.

| Sequence | ID |
|---|---|
| 5'-cccaagcttggcgcggagatgggggtgca-3' | SEQ ID NO:1 |
| 5'-cggatccgtcccctgtcctgcaggcct-3' | SEQ ID NO:2 |
| 5'-gagcgcaaatgttgtgtcga-3' | SEQ ID NO:3 |
| 5'-ggaattctcatttacccggagacaggga-3' | SEQ ID NO:4 |
| 5'-tggttttctcgatggaggctgggaggcct-3' | SEQ ID NO:5 |
| 5'-aggcctcccagcctccatcgagaaaacca-3' | SEQ ID NO:6 |
| 5'-cggatccggtggcggttccggtggaggcggaagcggcggtggaggatcagagcgcaaatgttgtgtcga-3' | SEQ ID NO:7 |
| 5'-gagtccaaatatggtccccca-3' | SEQ ID NO:8 |
| 5'-ggaattctcatttacccagagacaggga-3' | SEQ ID NO:9 |
| 5'-cctgagttcgcggggggacca-3' | SEQ ID NO:10 |
| 5'-gagtccaaatatggtcccccatgcccaccatgcccagcacctgagttcgcggggggacca-3' | SEQ ID NO:11 |

TABLE 1-continued

Sequences of Oligonucleotides.

| | |
|---|---|
| 5'-cggatccggtggcggttccggtggaggcggaagcggcggtggaggatcagag tccaaatatggtccccca-3' | SEQ ID NO:12 |
| 5'-gacaaaactcacacatgccca-3' | SEQ ID NO:13 |
| 5'-acctgaagtcgcgggggaccgt-3' | SEQ ID NO:14 |
| 5'-gacaaaactcacacatgcccaccgtgcccagcacctgaagtcgcgggggac cgt-3' | SEQ ID NO:15 |
| 5'-cggatccggtggcggttccggtggaggcggaagcggcggtggaggatcagac aaaactcacacatgccca-3' | SEQ ID NO:16 |

The invention claimed is:

1. A recombinant HuEPO-L-vFc fusion protein consisting of HuEPO, a peptide linker, and a human IgG Fc variant, wherein the human IgG Fc variant consists of a hinge, CH2, and CH3 domains of human IgG1 with Leu234Val, Leu235Ala, and Pro331Ser mutations of SEQ ID NO: 22.

2. The recombinant HuEPO-L-vFc fusion protein of claim 1, wherein the peptide linker which contains 20 or fewer amino acids is present between HuEPO and the human IgG Fc variant; and the peptide linker comprises two or more amino acids selected from the group consisting of glycine, serine, alanine, and threonine.

3. The HuEPO-L-vFc fusion protein of claim 1 which exhibits an enhanced in vitro biological activity of at least 2 fold relative to that of rHuEPO on a molar basis.

4. A CHO cell line transfected with DNA encoding the recombinant_HuEPO-L-vFc fusion protein of claim 1, wherein said recombinant fusion protein is expressed in its growth medium in excess of 10 μg per million cells in a 24 hour period.

5. The CHO cell line transfected with DNA encoding the recombinant HuEPO-L-vFc fusion protein of claim 4, wherein said recombinant fusion protein is expressed in its growth medium in excess of 30 μg per million cells in a 24 hour period.

6. A CHO cell line transfected with DNA encoding the recombinant HuEPO-L-vFc fusion protein of claim 1, wherein the human IgG Fc variant consists of a hinge, CH2, and CH3 domains of human IgG1 with Leu234Val, Leu235Ala, and Pro331Ser mutations of SEQ ID NO: 22, a flexible peptide linker which contains 20 or fewer amino acids is present between HuEPO and human IgG Fc variant, and the HuEPO-L-vFc fusion protein exhibits an enhanced in vitro biological activity of at least 2 fold relative to that of rHuEPO on a molar basis.

7. A method for making a recombinant fusion protein consisting of HuEPO, a flexible peptide linker, and a human IgG Fc variant, wherein the human IgG Fc variant consists of a hinge, CH2, and CH3 domains of human IgG1 with Leu234Val, Leu235Ala, and Pro331Ser mutations of SEQ ID NO: 22, wherein said methods comprises: (a) generating a CHO cell line transfected with DNA encoding the recombinant HuEPO-L-vFc fusion protein; (b) growing the cell line under conditions wherein the recombinant fusion protein is expressed in its growth medium in excess of 10 μg per million cells in a 24 hour period; and (c) purifying the expressed protein from/step (b), wherein the recombinant fusion protein exhibits an enhanced in vitro biological activity of at least 2 fold relative to that of rHuEPO on a molar basis.

8. The method of claim 7, wherein step (b) is in excess of 30 μg per million cells in a 24 hour period.

9. The method of claim 7, wherein the flexible peptide linker which contains 20 or fewer amino acids is present between HuEPO and the human IgG Fc variant; and the peptide linker comprises two or more amino acids selected from the group consisting of glycine, serine, alanine, and threonine.

10. The method of claim 9, wherein step (b) is in excess of 30 μg per million cells in a 24 hour period.

11. The method of claim 7, wherein step (b) is in excess of 30 μg per million cells in a 24 hour period.

12. A method for making a recombinant fusion protein consisting of HuEPO, a flexible peptide linker, and a human IgG Fc variant, wherein said method comprises: (a) generating a CHO cell line transfected with DNA encoding the recombinant HuEPO-L-vFc fusion protein; (b) growing the cell line under conditions wherein the recombinant fusion protein is expressed in its growth medium in excess of 10 μg per million cells in a 24 hour period; and (c) purifying the expressed recombinant fusion protein from step (b), wherein the recombinant fusion protein exhibits an enhanced in vitro biological activity of at least 2 fold relative to that of rHuEPO on a molar basis; wherein the flexible peptide linker which contains 20 or fewer amino acids is present between HuEPO and the human IgG Fc variant; and the peptide linker comprises two or more amino acids selected from the group consisting of glycine, serine, alanine, and threonine; wherein the human IgG Fc variant consists of a hinge, CH2, and CH3 domains and human IgG1 with Leu234Val, Leu235Ala, and Pro331Ser mutations of SEQ ID NO: 22.

* * * * *

SEQUENCE LISTING

<160> NUMBER OF SEQ ID NOS: 28

<210> SEQ ID NO 1
<211> LENGTH: 29
<212> TYPE: DNA
<213> ORGANISM: Artificial Sequence
<220> FEATURE:
<223> OTHER INFORMATION: PCR primer

<400> SEQUENCE: 1
cccaagcttg gcgcggagat ggggggtgca                29

<210> SEQ ID NO 2
<211> LENGTH: 27
<212> TYPE: DNA
<213> ORGANISM: Artificial sequence
<220> FEATURE:
<223> OTHER INFORMATION: PCR primer

<400> SEQUENCE: 2
cggatccgtc ccctgtcctg caggcct                   27

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
gagcgcaaat gttgtgtcga                           20

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
ggaattctca tttacccgga gacaggga                  28

<210> SEQ ID NO 5
<211> LENGTH: 29

<212> TYPE: DNA
<213> ORGANISM: Artificial Sequence
<220> FEATURE:
<223> OTHER INFORMATION: PCR primer

<400> SEQUENCE: 5
tggttttctc gatggaggct gggaggcct                                29

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
aggcctccca gcctccatcg agaaaacca                                29

<210> SEQ ID NO 7
<211> LENGTH: 69
<212> TYPE: DNA
<213> ORGANISM: Artificial Sequence
<220> FEATURE:
<223> OTHER INFORMATION: PCR primer

<400> SEQUENCE: 7
cggatccggt ggcggttccg gtggaggcgg aagcggcggt ggaggatcag agcgcaaatg    60
ttgtgtcga                                                          69

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
gagtccaaat atggtccccc a                                        21

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
ggaattctca tttacccaga gacaggga                                 28

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cctgagttcg cggggggacc a                                        21

<210> SEQ ID NO 11
<211> LENGTH: 60
<212> TYPE: DNA
<213> ORGANISM: Artificial Sequence
<220> FEATURE:
<223> OTHER INFORMATION: PCR primer

```
<400> SEQUENCE: 11
gagtccaaat atggtccccc atgcccacca tgcccagcac ctgagttcgc gggggggacca    60

<210> SEQ ID NO 12
<211> LENGTH: 70
<212> TYPE: DNA
<213> ORGANISM: Artificial Sequence
<220> FEATURE:
<223> OTHER INFORMATION: PCR primer

<400> SEQUENCE: 12
cggatccggt ggcggttccg gtggaggcgg aagcggcggt ggaggatcag agtccaaata    60
tggtccccca                                                           70

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
gacaaaactc acacatgccc a                                              21

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
acctgaagtc gcggggggac cgt                                            23

<210> SEQ ID NO 15
<211> LENGTH: 55
<212> TYPE: DNA
<213> ORGANISM: Artificial Sequence
<220> FEATURE:
<223> OTHER INFORMATION: PCR primer

<400> SEQUENCE: 15
gacaaaactc acacatgccc accgtgccca gcacctgaag tcgcgggggg accgt         55

<210> SEQ ID NO 16
<211> LENGTH: 70
<212> TYPE: DNA
<213> ORGANISM: Artificial Sequence
<220> FEATURE:
<223> OTHER INFORMATION: PCR primer

<400> SEQUENCE: 16
cggatccggt ggcggttccg gtggaggcgg aagcggcggt ggaggatcag acaaaactca    60
cacatgccca                                                           70

<210> SEQ ID NO 17
<211> LENGTH: 1332
<212> TYPE: DNA
<213> ORGANISM: Artificial Sequence
<220> FEATURE:
<223> OTHER INFORMATION: HuEPO-L-vFc gamma2 (Figure 2A)

<400> SEQUENCE: 17
aagcttggcg cggagatggg ggtgcacgaa tgtcctgcct ggctgtggct tctcctgtcc    60
```

-continued

```
ctgctgtcgc tccctctggg cctcccagtc ctgggcgccc caccacgcct catctgtgac      120
agccgagtcc tggagaggta cctcttggag gccaaggagg ccgagaatat cacgacgggc      180
tgtgctgaac actgcagctt gaatgagaat atcactgtcc cagacaccaa agttaatttc      240
tatgcctgga gaggatgga ggtcgggcag caggccgtag aagtctggca gggcctggcc       300
ctgctgtcgg aagctgtcct gcggggccag gccctgttgg tcaactcttc ccagccgtgg      360
gagcccctgc agctgcatgt ggataaagcc gtcagtggcc ttcgcagcct caccactctg      420
cttcgggctc tggagccca gaaggaagcc atctcccctc cagatgcggc ctcagctgct       480
ccactccgaa caatcactgc tgacactttc cgcaaactct ccgagtctac tccaatttc      540 ctccggggaa agctgaagct gtacacaggg gaggcctgca ggacagggga cggatccggt      600
ggcggttccg gtggaggcgg aagcggcggt ggaggatcag agcgcaaatg ttgtgtcgag      660
tgcccaccgt gcccagcacc acctgtggca ggaccgtcag tcttcctctt ccccccaaaa      720
cccaaggaca ccctcatgat ctcccggacc cctgaggtca cgtgcgtggt ggtggacgtg      780
agccacgaag accccgaggt ccagttcaac tggtacgtgg acggcgtgga ggtgcataat      840
gccaagacaa agccacggga ggagcagttc aacagcacgt ccgtgtggt cagcgtcctc       900 accgttgtgc accaggactg gctgaacggc aaggagtaca gtgcaaggt ctccaacaaa       960 ggcctcccag cctccatcga gaaaaccatc tccaaaacca agggcagcc cgagaacca      1020 caggtgtaca ccctgccccc atcccgggag gagatgacca gaaccaggt cagcctgacc     1080 tgcctggtca aaggcttcta ccccagcgac atcgccgtgg agtgggagag caatgggcag     1140
ccggagaaca actacaagac cacacctccc atgctggact ccgacggctc cttcttcctc     1200
tacagcaagc tcaccgtgga caagagcagg tggcagcagg ggaacgtctt ctcatgctcc     1260
gtgatgcatg aggctctgca caaccactac acgcagaaga gcctctccct gtctccgggt    1320
aaatgagaat tc                                                         1332
```

<210> SEQ ID NO 18
<211> LENGTH: 436
<212> TYPE: PRT
<213> ORGANISM: Artificial Sequence
<220> FEATURE:
<223> OTHER INFORMATION: HuEPO-L-vFc gamma2 with a 27-amino acid leader peptide (Figure 2A)

<400> SEQUENCE: 18

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125
```

-continued

```
Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Gly Ser Gly Gly Gly Ser Gly Gly Gly Ser Gly Gly Gly Gly Ser
            195                 200                 205

Glu Arg Lys Cys Cys Val Glu Cys Pro Pro Cys Pro Ala Pro Pro Val
        210                 215                 220

Ala Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Gln Phe Asn Trp Tyr Val Asp Gly Val Glu
            260                 265                 270

Val His Asn Ala Lys Thr Lys Pro Arg Glu Glu Gln Phe Asn Ser Thr
        275                 280                 285

Phe Arg Val Val Ser Val Leu Thr Val Val His Gln Asp Trp Leu Asn
290                 295                 300

Gly Lys Glu Tyr Lys Cys Lys Val Ser Asn Lys Gly Leu Pro Ala Ser
305                 310                 315                 320

Ile Glu Lys Thr Ile Ser Lys Thr Lys Gly Gln Pro Arg Glu Pro Gln
                325                 330                 335

Val Tyr Thr Leu Pro Pro Ser Arg Glu Met Thr Lys Asn Gln Val
            340                 345                 350

Ser Leu Thr Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
370                 375                 380

Pro Met Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys
        435
```

<210> SEQ ID NO 19
<211> LENGTH: 1335
<212> TYPE: DNA
<213> ORGANISM: Artificial Sequence
<220> FEATURE:
<223> OTHER INFORMATION: HuEPO-L-vFc gamma4 (Figure 2B)

<400> SEQUENCE: 19

```
aagcttggcg cggagatggg ggtgcacgaa tgtcctgcct ggctgtggct tctcctgtcc      60
ctgctgtcgc tccctctggg cctcccagtc ctgggcgccc caccacgcct catctgtgac     120
agccgagtcc tggagaggta cctcttggag gccaaggagg ccgagaatat cacgacgggc     180
tgtgctgaac actgcagctt gaatgagaat atcactgtcc cagacaccaa agttaatttc     240
```

```
tatgcctgga agaggatgga ggtcgggcag caggccgtag aagtctggca gggcctggcc        300
ctgctgtcgg aagctgtcct gcggggccag gccctgttgg tcaactcttc ccagccgtgg        360
gagcccctgc agctgcatgt ggataaagcc gtcagtggcc ttcgcagcct caccactctg        420
cttcgggctc tgggagccca agggaagcc atctcccctc cagatgcggc ctcagctgct        480
ccactccgaa caatcactgc tgacactttc cgcaaactct ccgagtcta ctccaatttc         540
ctccggggaa agctgaagct gtacacaggg gaggcctgca ggacagggga cggatccggt        600
ggcggttccg gtggaggcgg aagcggcggt ggaggatcag agtccaaata tggtccccca        660
tgcccaccat gcccagcacc tgagttcgcg ggggaccat cagtcttcct gttccccca          720
aaacccaagg acactctcat gatctcccgg accctgagg tcacgtgcgt ggtggtggac         780
gtgagccagg aagaccccga ggtccagttc aactggtacg tggatggcgt ggaggtgcat        840
aatgccaaga caaagccgcg ggaggagcag ttcaacagca cgtaccgtgt ggtcagcgtc        900
ctcaccgtcc tgcaccagga ctggctgaac ggcaaggagt acaagtgcaa ggtctccaac        960
aaaggcctcc cgtcctccat cgagaaaacc atctccaaag ccaaagggca gccccgagag       1020
ccacaggtgt acaccctgcc cccatcccag gaggagatga ccaagaacca ggtcagcctg       1080
acctgcctgg tcaaaggctt ctaccccagc gacatcgccg tggagtggga gagcaatggg       1140
cagccggaga caactacaa gaccacgcct cccgtgctgg actccgacgg ctccttcttc        1200
ctctacagca ggctaaccgt ggacaagagc aggtggcagg aggggaatgt cttctcatgc       1260
tccgtgatgc atgaggctct gcacaaccac tacacacaga gagcctctc cctgtctctg       1320
ggtaaatgag aattc                                                        1335
```

<210> SEQ ID NO 20
<211> LENGTH: 437
<212> TYPE: PRT
<213> ORGANISM: Artificial Sequence
<220> FEATURE:
<223> OTHER INFORMATION: HuEPO-L-vFc gamma4 with a 27-amino acid leader peptide (Figure 2B)

<400> SEQUENCE: 20

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160
```

```
Thr Ala Asp Thr Phe Arg Lys Leu Phe Arg Val Tyr Ser Asn Phe Leu
            165                 170                 175
Arg Gly Lys Leu Lys Leu Tyr Thr Gly Glu Ala Cys Arg Thr Gly Asp
            180                 185                 190
Gly Ser Gly Gly Ser Gly Gly Gly Ser Gly Gly Gly Ser
            195                 200                 205
Glu Ser Lys Tyr Gly Pro Pro Cys Pro Pro Cys Pro Ala Pro Glu Phe
    210                 215                 220
Ala Gly Gly Pro Ser Val Phe Leu Phe Pro Pro Lys Pro Lys Asp Thr
225                 230                 235                 240
Leu Met Ile Ser Arg Thr Pro Glu Val Thr Cys Val Val Val Asp Val
                245                 250                 255
Ser Gln Glu Asp Pro Glu Val Gln Phe Asn Trp Tyr Val Asp Gly Val
        260                 265                 270
Glu Val His Asn Ala Lys Thr Lys Pro Arg Glu Glu Gln Phe Asn Ser
    275                 280                 285
Thr Tyr Arg Val Val Ser Val Leu Thr Val Leu His Gln Asp Trp Leu
290                 295                 300
Asn Gly Lys Glu Tyr Lys Cys Lys Val Ser Asn Lys Gly Leu Pro Ser
305                 310                 315                 320
Ser Ile Glu Lys Thr Ile Ser Lys Ala Lys Gly Gln Pro Arg Glu Pro
                325                 330                 335
Gln Val Tyr Thr Leu Pro Pro Ser Gln Glu Glu Met Thr Lys Asn Gln
        340                 345                 350
Val Ser Leu Thr Cys Leu Val Lys Gly Phe Tyr Pro Ser Asp Ile Ala
    355                 360                 365
Val Glu Trp Glu Ser Asn Gly Gln Pro Glu Asn Asn Tyr Lys Thr Thr
    370                 375                 380
Pro Pro Val Leu Asp Ser Asp Gly Ser Phe Phe Leu Tyr Ser Arg Leu
385                 390                 395                 400
Thr Val Asp Lys Ser Arg Trp Gln Glu Gly Asn Val Phe Ser Cys Ser
                405                 410                 415
Val Met His Glu Ala Leu His Asn His Tyr Thr Gln Lys Ser Leu Ser
        420                 425                 430
Leu Ser Leu Gly Lys
        435
```

<210> SEQ ID NO 21
<211> LENGTH: 1329
<212> TYPE: DNA
<213> ORGANISM: Artificial Sequence
<220> FEATURE:
<223> OTHER INFORMATION: HuEPO-L-vFc gamma1 (Figure 2C)

<400> SEQUENCE: 21

```
aagcttggcg cggagatggg ggtgcacgaa tgtcctgcct ggctgtggct tctcctgtcc    60
ctgctgtcgc tccctctggg cctcccagtc ctgggcgccc caccacgcct catctgtgac   120
agccgagtcc tggagaggta cctcttggag gccaaggagg ccgagaatat cacgacgggc   180
tgtgctgaac actgcagctt gaatgagaat atcactgtcc cagacaccaa agttaatttc   240
tatgcctgga gaggatgga ggtcgggcag caggccgtag aagtctggca gggcctggcc   300
ctgctgtcgg aagctgtcct gcggggccag gccctgttgg tcaactcttc ccagccgtgg   360
gagcccctgc agctgcatgt ggataaagcc gtcagtggcc ttcgcagcct caccactctg   420
cttcgggctc tgggagccca gaaggaagcc atctcccctc agatgcggc ctcagctgct   480
```

```
ccactccgaa caatcactgc tgacactttc cgcaaactct tccgagtcta ctccaatttc      540
ctccggggaa agctgaagct gtacacaggg gaggcctgca ggacagggga cggatccggt      600
ggcggttccg gtggaggcgg aagcggcggt ggaggatcag acaaaactca cacatgccca      660
ccgtgcccag cacctgaagt cgcgggggga ccgtcagtct tcctcttccc cccaaaaccc      720
aaggacaccc tcatgatctc ccggacacct gaggtcacat gcgtggtggt ggacgtgagc      780
cacgaagacc ctgaggtcaa gttcaactgg tacgtggacg gcgtggaggt gcataatgcc      840
aagacaaagc cgcgggagga gcagtacaac agcacgtacc gggtggtcag cgtcctcacc      900
gtcctgcacc aggactggct gaatggcaag gagtacaagt gcaaggtctc caacaaagcc      960
ctcccagcct ccatcgagaa aaccatctcc aaagccaaag gcagccccg agaaccacag      1020 gtgtacaccc tgcccccatc ccgggatgag ctgaccaaga accaggtcag cctgacctgc      1080
ctggtcaaag gcttctatcc cagcgacatc gccgtggagt gggagagcaa tgggcagccg      1140
gagaacaact acaagaccac gcctcccgtg ctggactccg acggctcctt cttcctctac      1200
agcaagctca ccgtggacaa gagcaggtgg cagcagggga acgtcttctc atgctccgtg      1260
atgcatgagg ctctgcacaa ccactacacg cagaagagcc tctccctgtc tccgggtaaa      1320
tgagaattc                                                              1329
```

<210> SEQ ID NO 22
<211> LENGTH: 435
<212> TYPE: PRT
<213> ORGANISM: Artificial Sequence
<220> FEATURE:
<223> OTHER INFORMATION: HuEPO-L-vFc gamma1 with a 27-amino acid leader peptide (Figure 2C)

<400> SEQUENCE: 22

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Gly Ser Gly Gly Gly Ser Gly Gly Gly Gly Ser Gly Gly Gly Gly Ser
```

```
            195                 200                 205
Asp Lys Thr His Thr Cys Pro Pro Cys Pro Ala Pro Glu Val Ala Gly
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Ser Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 23
<211> LENGTH: 16
<212> TYPE: PRT
<213> ORGANISM: Artificial Sequence
<220> FEATURE:
<223> OTHER INFORMATION: synthetic sequence

<400> SEQUENCE: 23

Gly Ser Gly Gly Gly Ser Gly Gly Gly Ser Gly Gly Gly Gly Ser
1               5                   10                  15

<210> SEQ ID NO 24
<211> LENGTH: 15
<212> TYPE: PRT
<213> ORGANISM: Human IgG1 hinge sequence

<400> SEQUENCE: 24

Glu Pro Lys Ser Cys Asp Lys Thr His Thr Cys Pro Pro Cys Pro
1               5                   10                  15

<210> SEQ ID NO 25
<211> LENGTH: 10
<212> TYPE: PRT
<213> ORGANISM: Truncated human IgG1 hinge sequence

<400> SEQUENCE: 25
```

```
Asp Lys Thr His Thr Cys Pro Pro Cys Pro
1               5                  10
```

<210> SEQ ID NO 26
<211> LENGTH: 232
<212> TYPE: PRT
<213> ORGANISM: Human IgG1 Fc with native hinge, CH2 and CH3 domains

<400> SEQUENCE: 26

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 27
<211> LENGTH: 228
<212> TYPE: PRT
<213> ORGANISM: Human IgG2 Fc with native hinge, CH2 and CH3 domains

<400> SEQUENCE: 27

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80
```

```
Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225
```

<210> SEQ ID NO 28
<211> LENGTH: 229
<212> TYPE: PRT
<213> ORGANISM: Human IgG4 Fc with native hinge, CH2 and CH3 domains

<400> SEQUENCE: 28

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205
```

```
-continued

Val Met His Glu Ala Leu His Asn His Tyr Thr Gln Lys Ser Leu Ser
    210                 215                 220

Leu Ser Leu Gly Lys
225
```